(12) United States Patent
Chan et al.

(10) Patent No.: US 12,232,848 B2
(45) Date of Patent: Feb. 25, 2025

(54) SYSTEM AND METHOD OF FACIAL ANALYSIS

(71) Applicant: Neumora Therapeutics, Inc., Brisbane, CA (US)

(72) Inventors: John Chan, Boston, MA (US); Sandeep R. Datta, Cambridge, MA (US); Alexander B. Wiltschko, Somerville, MA (US)

(73) Assignee: NEUMORA THERAPEUTICS, INC., Brisbane, CA (US)

( * ) Notice: Subject to any disclaimer, the term of this patent is extended or adjusted under 35 U.S.C. 154(b) by 422 days.

(21) Appl. No.: 17/603,779

(22) PCT Filed: Apr. 29, 2020

(86) PCT No.: PCT/US2020/030431
§ 371 (c)(1),
(2) Date: Oct. 14, 2021

(87) PCT Pub. No.: WO2020/223324
PCT Pub. Date: Nov. 5, 2020

(65) Prior Publication Data
US 2022/0101655 A1 Mar. 31, 2022

Related U.S. Application Data

(60) Provisional application No. 62/840,076, filed on Apr. 29, 2019.

(51) Int. Cl.
*G06V 40/16* (2022.01)
*A61B 5/00* (2006.01)
(Continued)

(52) U.S. Cl.
CPC .......... *A61B 5/0077* (2013.01); *G06T 7/0012* (2013.01); *G06T 7/70* (2017.01);
(Continued)

(58) Field of Classification Search
CPC ..... A61B 5/0077; A61B 5/165; A61B 5/4824; A61B 5/7267; G06T 7/0012; G06T 7/70;
(Continued)

(56) References Cited

U.S. PATENT DOCUMENTS 7,742,623 B1 * 6/2010 Moon ................... G06V 40/19
382/103
8,219,438 B1 7/2012 Moon et al.
(Continued)

OTHER PUBLICATIONS

Extended European Search Report for EP Application No. 20799454.2, mailed Dec. 14, 2022, 10 pp.
(Continued)

*Primary Examiner* — Siamak Harandi
(74) *Attorney, Agent, or Firm* — NIXON PEABODY LLP

(57) ABSTRACT

A system for facial analysis includes a camera, a data storage device and a data processing system. The camera takes video of a subject's face, and the data storage device receives and stores the video. The data processing system extracts a pose of the subject's face, and a representation of the subject's facial gesture state. The pose includes the angle and position of the subject's face. The representation includes facial keypoints that are a collection of points on the subject's face. The system then concatenates each data stream to align the data streams in time, extracts a plurality of facial syllables from the aligned data streams, and compiles the facial syllables into a series of state sequences. Based on the series of state sequences, the system extracts a behavioral fingerprint for the subject that provides a summary of the subject's state over a given period of time.

31 Claims, 13 Drawing Sheets

(51) Int. Cl.
*G06T 7/00* (2017.01)
*G06T 7/70* (2017.01)
*G06V 10/764* (2022.01)
*G06V 10/82* (2022.01)
*G06V 40/20* (2022.01)

(52) U.S. Cl.
CPC ............ *G06V 10/764* (2022.01); *G06V 10/82* (2022.01); *G06V 40/161* (2022.01); *G06V 40/171* (2022.01); *G06V 40/174* (2022.01); *G06V 40/176* (2022.01); *G06V 40/20* (2022.01); *G06T 2207/10016* (2013.01); *G06T 2207/30201* (2013.01)

(58) Field of Classification Search
CPC .......... G06T 2207/10016; G06T 2207/30201; G06V 10/764; G06V 10/82; G06V 40/161; G06V 40/171; G06V 40/174; G06V 40/176; G06V 40/20; G06F 16/783; G06F 21/32; G16H 30/40; G16H 50/20
See application file for complete search history.

(56) References Cited

U.S. PATENT DOCUMENTS

| | | |
|---|---|---|
| 2011/0263946 A1 | 10/2011 | el Kaliouby et al. |
| 2013/0172691 A1 | 7/2013 | Tran |
| 2017/0238859 A1 | 8/2017 | Sadowsky et al. |
| 2017/0286759 A1 | 10/2017 | Yao et al. |

OTHER PUBLICATIONS

International Search Report in International Application No. PCT/US2020/030431, mailed Jul. 16, 2020, 2 pp.
Written Opinion in International Application No. PCT/US2020/030431, mailed Jul. 16, 2020, 7 pp.

* cited by examiner

Extracting Neural Network Features Over Time

SYSTEM AND METHOD OF FACIAL ANALYSIS

PRIORITY

This patent application is a 35 U.S.C. § 371 national stage filing of International Application No. PCT/US2020/030431, filed on Apr. 29, 2020, which in turn claims priority from U.S. Provisional Application No. 62/840,076, filed Apr. 29, 2019, entitled "System and Method of Facial Analysis," and naming John Chan, Sandeep R. Datta and Alexander B. Wiltschko as inventors. The entire contents of each of the foregoing applications are incorporated herein by reference.

TECHNICAL FIELD

The present invention relates to facial analysis systems and methods, and more particularly to system and methods that characterize the unique states that a face can exhibit.

BACKGROUND ART

The human face and the expression on that face provide significant insight into the state of an individual. For example, facial expressions and the locations of the various features on the face show whether an individual is happy, sad, in pain, the level of pain (e.g., on a pain scale), etc. The ability to analyze facial features and predict possible changes in the individual's state may be beneficial in a number of areas.

SUMMARY OF THE EMBODIMENTS

In accordance with some embodiments of the present invention, a system for facial analysis includes a camera (e.g., a two-dimensional or three-dimensional camera), a data storage device and a data processing system. The camera takes one or more videos (each having a plurality of frames) of a subject's face. The data storage device receives and stores the video. The data processing system may have a processor and program. The processing system may extract a pose of the subject's face and a representation of the subject's facial gesture state. The pose may include the angle and position of the subject's face and the representation of the gesture state may include facial keypoints (e.g., subject's nose, mouth, eyes and jaw line) that are a collection of points on the subject's face. The system may then concatenate each data stream to align the data streams in time, extract a plurality of facial syllables from the aligned data streams, and compile the plurality of facial syllables into a series of state sequences. Based on this information (e.g., the series of state sequences), the system may extract a behavioral fingerprint for the subject. The behavioral fingerprint may provide a summary of the subject's state over a given period of time.

In some embodiments, the data processing system may also have program code that extracts face regions from each of the frames of the video prior to extracting the pose of the subject's face. The data processing system may use latent embeddings derived from artificial neural networks and/or deep learning models to extract the facial gesture state(s). Additionally or alternatively, the processing system may analyze the videos in aggregate to extract the facial syllables. The system may also predict, based on the behavioral fingerprint, a level of pain, a level of anxiety, a level of depression, a level of hunger, a level of satiety, and/or a level of fatigue and/or classify the behavioral summary as a pre-event summary or a post event summary.

In accordance with further embodiments, a method of facial analysis may include recording a video of a subject's face using a camera (e.g., a two dimensional or three dimensional camera), and storing the video in a data storage device. The video may have a plurality of frames and the method may extract a pose of the subject's face, for example, including the angle and position of the subject's face. The method may then extract a representation of the subject's facial gesture state, and concatenate each data stream to align them in time. The representation of the facial gesture state may include facial keypoints (e.g., the subject's nose, mouth, eyes and/or jaw line) that are a collection of points on the subject's face. The method may then (1) extract a plurality of facial syllables from the aligned data streams, (2) compile the plurality of facial syllables into a series of state sequences, and (3) extract a behavioral fingerprint for the subject based on the series of state sequences. The behavioral fingerprint may provide a summary of the subject's state over a given period of time.

In some embodiments, the method may include extracting a face region from each of the frames of the video prior to extracting the pose of the subject's face. Additionally or alternatively, the method may use latent embedding derived from artificial neural networks and/or deep learning to extract the facial gesture state and/or extracting the facial syllable may include analyzing the videos in aggregate. The method may also predict, based on the behavioral fingerprint, a level of pain, a level of anxiety, a level of depression, a level of hunger, a level of satiety, and/or a level of fatigue. The method may also classify the behavioral summary as a pre-event summary or a post event summary.

In accordance with additional embodiments, a system for subject analysis includes a camera (e.g., a two dimensional or three dimensional camera), a data storage device, and a data processing system. The camera may take video (having multiple frames) of a portion of a subject. The data storage device may receive and store the video. The data processing system may have a processor and program code which when executed extracts a pose of the portion of the subject. The pose may include the angle and position of the portion of the subject. The program code may also extract a representation of the subject's gesture state and concatenate each data stream to align the streams in time. The representation may include keypoints that are a collection of points on the portion of the subject.

The program code may then extract a plurality of syllables from the aligned data streams, compile the plurality of syllables into a series of state sequences, and extract a behavioral fingerprint for the subject based on the series of state sequences. The behavioral fingerprint may provide a summary of the subject's state over a given period of time. The portion of the subject may be the subject's face, and the pose of the portion of the subject may be the pose of the subject's face. The pose may include the angle and position of the subject's face. The representation of the subject's gesture state may be a representation of the subject's facial gesture state, and the keypoints may be facial keypoints that are a collection of points on the subject's face and may include the subject's nose, mouth, eyes and/or jaw line. The plurality of syllables may be a plurality of facial syllables.

In some embodiments, the data processing system may use latent embeddings derived from artificial neural networks and/or deep learning models to extract the gesture state. Additionally or alternatively, the processing system may analyze videos in aggregate to extract the syllables and/or predict, based on the behavioral fingerprint, a level of pain, a level of anxiety, a level of depression, a level of hunger, a level of satiety, and/or a level of fatigue. The processing system may classify the behavioral summary as a pre-event summary or a post event summary. The data processing system may also have program code that extracts a region from each of the frames of the video prior to extracting the pose of the portion of the subject.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

In illustrative embodiments, a system automatically characterizes the nature and number of unique states (e.g., "facial syllables) a human face can exhibit from video recordings and without human bias. A collection of the discovered facial syllables may include four main components: the number of facial syllables, their grammatical structure (the transition structure between syllables), their content (i.e. what does the facial syllable look like), and their duration (how long they last). This information may then be used to predict a number of characteristics including, for example, pain level.

Figure 1:
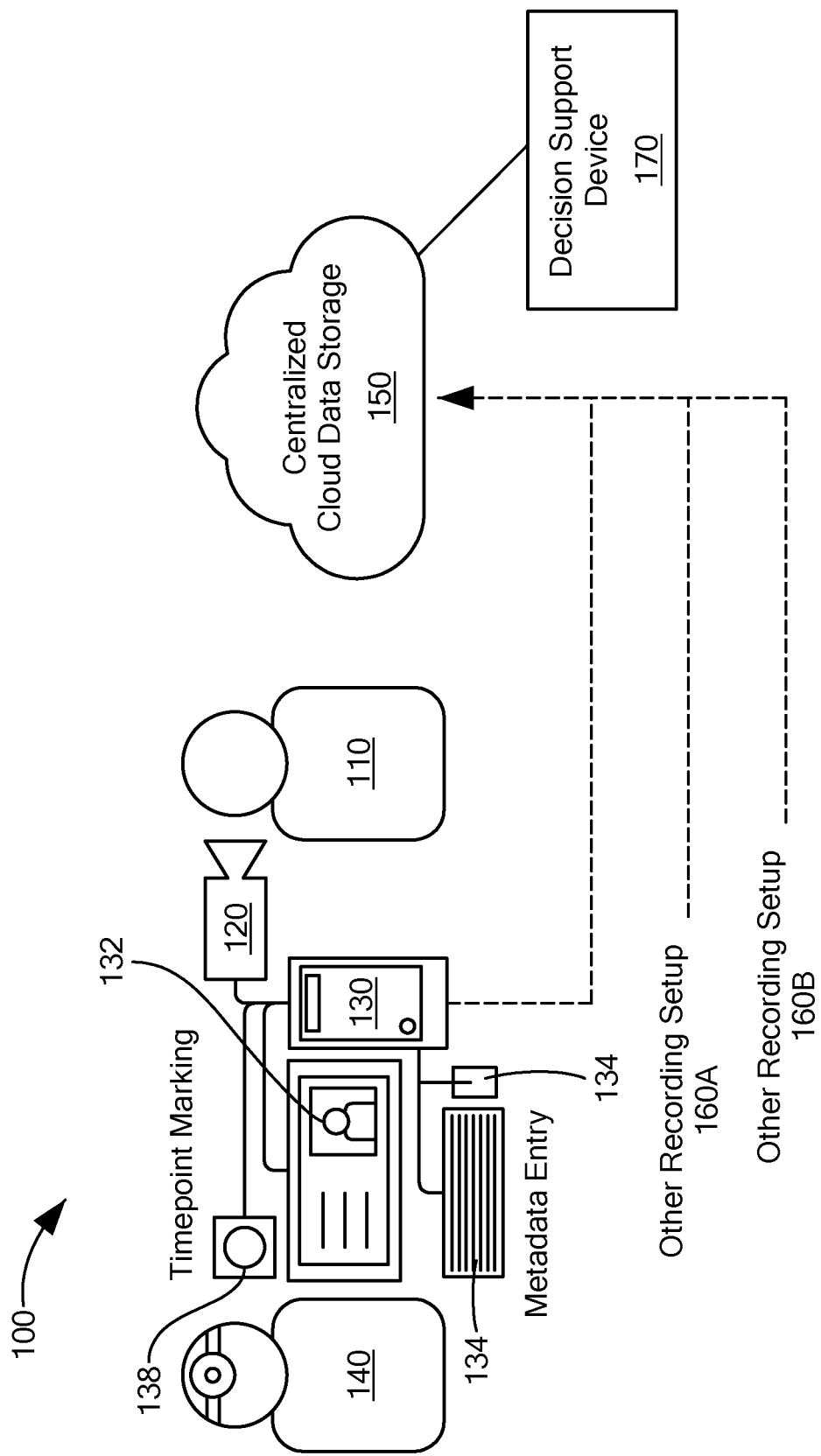
FIG. 1 schematically shows a facial analysis system in accordance with illustrative embodiments of the present invention.

FIG. 1 schematically shows a system 100 for analyzing the facial expressions of a patient/subject 110. The system 100 may include a camera 120 that takes images or video of the patient/subject over time and perhaps, as discussed in greater detail below, as the patient/subject is asked to perform various tasks and/or is exposed to various external stimuli (e.g., drugs, sound, light, questions, etc.). The camera 120 may be connected to a computer 130 or other processing device that saves and/or processes the recorded video and images. To allow the user 140 (e.g., a doctor or technician) to view the video/images and enter information related to the patient/subject, video/image, task, external stimuli, a reported level of pain, other metadata, etc., the computer 130 may include a monitor 132 and one or more input devices (e.g., a keyboard 136 and a mouse 134). For example, during use, the user 140 may use the input devices 134/136 to mark various points in the video such as when a task is performed by the patient or a drug is administered, when the patient reports pain starts/increases and/or when pain lessens or stops.

As noted above, in some embodiments, the video and images may be stored and processed locally on the computer 130. However, in other embodiments, the video and image data (or the data from the video/image processing by the computer 130) may be uploaded to a centralized data storage device 150 (e.g., a cloud based data storage system). Additionally, the video/images from other recording set-ups 160A/160B can similarly be uploaded to the centralized data storage device 150, where additional processing, aggregation and/or machine learning can occur. It should be noted that, although FIG. 1 only shows three recording systems 100/160A/160B uploading data to the centralized data storage system 150 any number of recording systems may upload data to the storage system 150.

In some embodiments, the system 100 may also have a decision support device 170 connected to the data storage device 150 and/or the computer 130. As discussed in greater detail below, based on the information determined by the system 100 and the determined facial expressions/changes in facial expressions (e.g., whether the subject 110 is in pain, the level of pain, the level of anxiety or fatigue experienced by the subject 100), the decision support device 170 may perform an assessment and determine an appropriate course of action. For example, the decision support device 170 may send output to a clinical trial evaluation system that may be used (e.g., by a medical lead) to assess drug efficacy. Alternatively, the decision support device 170 may output and alarm to alert a patient of a potential episode (e.g., in the case of Myasthenia Gravis), alert a driver that they are experiencing heightened anxiety of fatigue while driving, and/or trigger the start of a treatment for a dementia patient about to experience an anger episode.

The type of camera 120 may vary depending on the application. For example, in some applications a two-dimension black and white camera may be sufficient. However, in other applications, a three-dimensional, color, depth and/or infrared ("IR") camera may be useful and/or required. It should also be noted that the camera 150 may be mounted on a tri-pod or similar device or may be mounted directly to the patient/subject. For example, the camera 120 may be mounted on a device that is placed on the patient/subject's head. The camera 120 may free record the patient/subject or may only record while specific tasks are performed. Additionally or alternatively, the camera 120/system 100 may automatically detect when recording should start (e.g., based on specific time point, movement by the patient/subject, etc.) or the system 100 may include a button 138 that the user 140 presses to start and stop recording at the appropriate time. Furthermore, in telemedicine applications, the camera 120 may be on the subject's cell phone or home computer. In such embodiments, the cell phone or home computer may then send the video to the computer 130 and/or storage device 150

Figure 2:
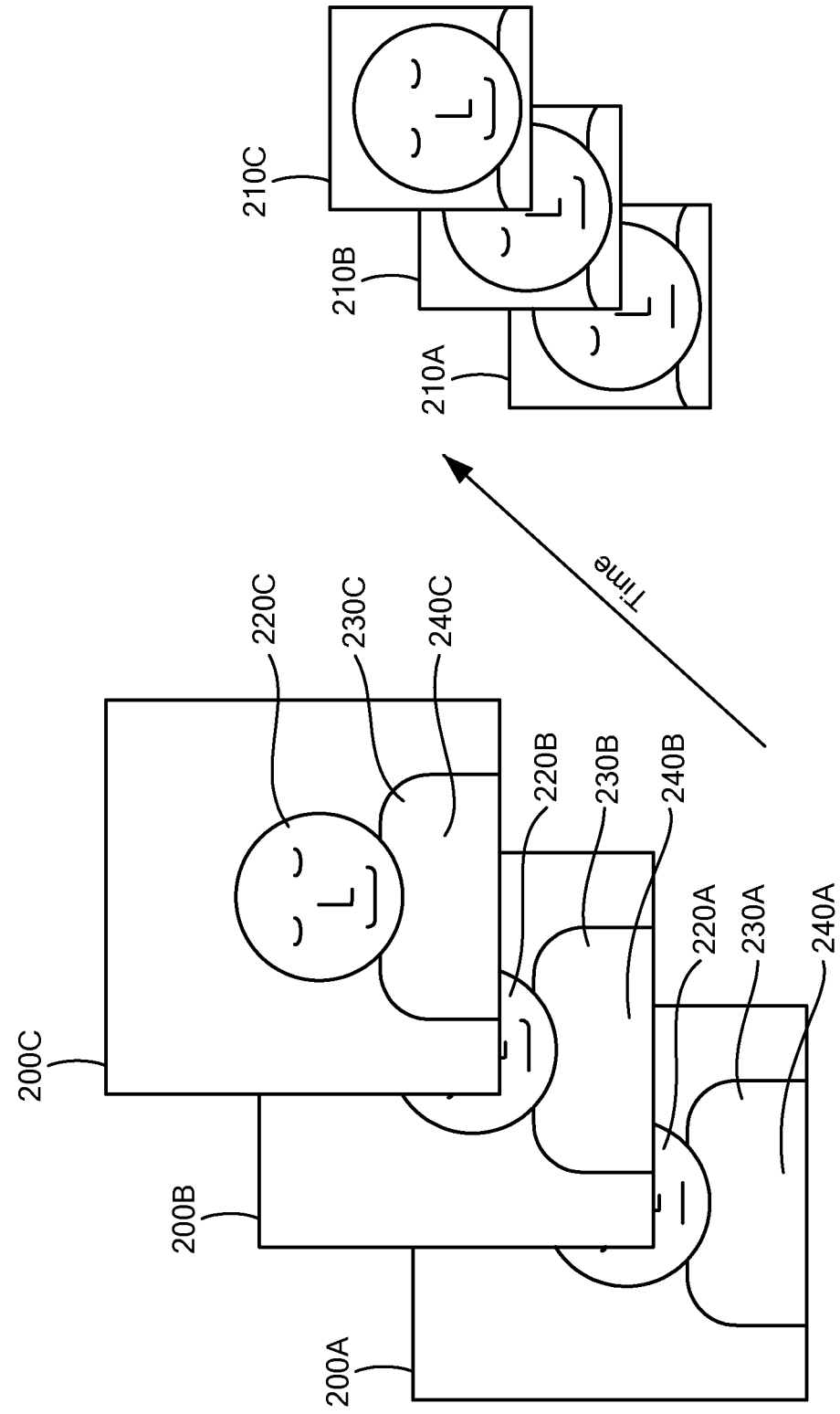
FIG. 2 schematically shows the extraction of facial regions from images/videos taken with the system shown in FIG. 1, in accordance with illustrative embodiments of the present invention.

During use, the camera 150 may first record the video of the patient/subject's face and forward the video data to the computer 130 and/or the centralized data storage device 150. As noted above, the camera 120 may automatically begin recording the video or may begin recording in response to the user 140 pressing a button 138 or otherwise starting the camera. Once the video is taken (or as the video is being taken), the system 100 may identify and extract the face region 220A/B/C from the individual images/frames 210A/B/C within the video stream. For example, as shown FIG. 2, the system 100 may identify only the face region from each of the starting video frames/images 200A/B/C and remove any unnecessary background image data and/or other portions of the patient/subject 110 (e.g., their shoulder 230A/B/C and chest area 240A/B/C) from the images/frames 200A/B/C. Additionally or alternatively, the system may also extract the pose of the patient/subject's face (e.g., the angle and position of the face) and extract the eye gaze of the patient/subject (e.g., the direction the subject's eyes are facing relative to the head pose). Based on some or all of this extracted data/information, the system may create/generate a face region image 210A/B/C for each of the starting/incoming video frames/images. If necessary and depending on the pose and the eye gaze, the system may normalize the face region images 210A/B/C to accommodate for the variations in the facial pose and eye gaze from image to image.

Figure 3A:
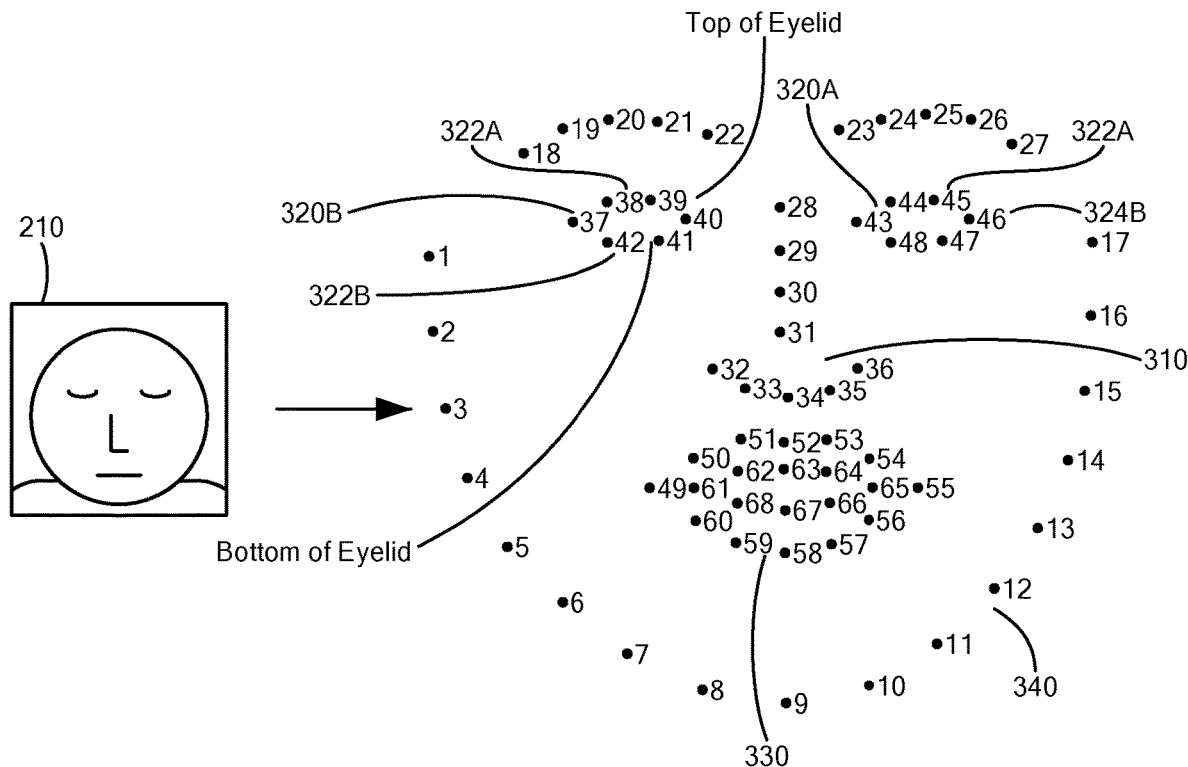
FIGS. 3A-3D schematically show the extraction of facial keypoints from images/videos taken with the system shown in FIG. 1, in accordance with illustrative embodiments of the present invention.
Figure 3B:
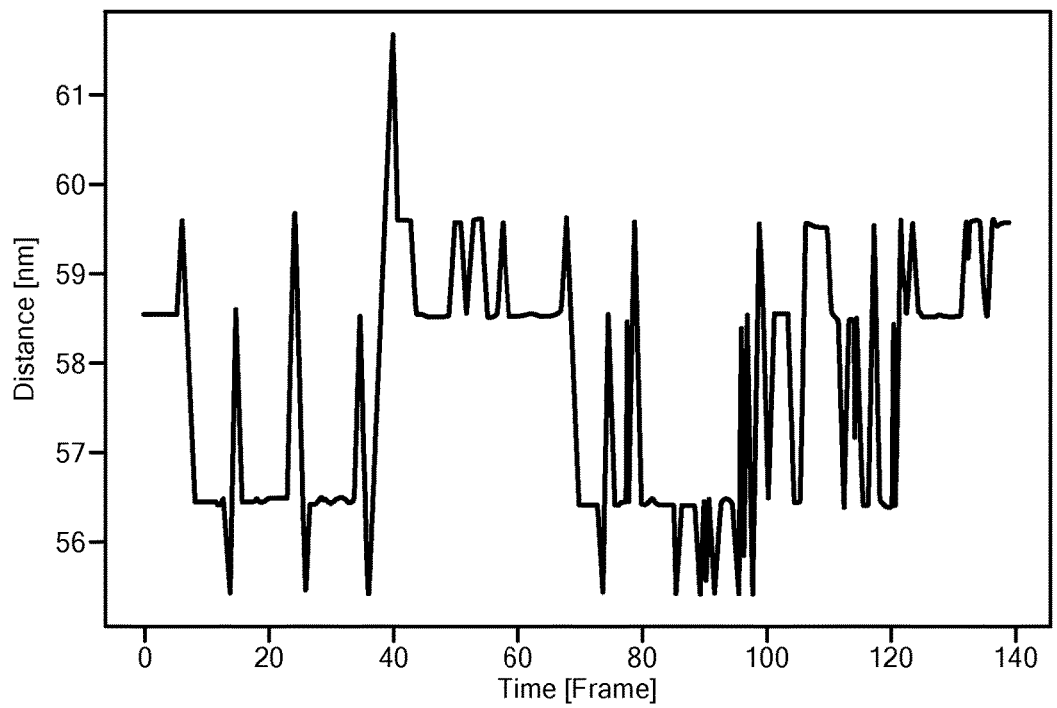
Figure 3C:
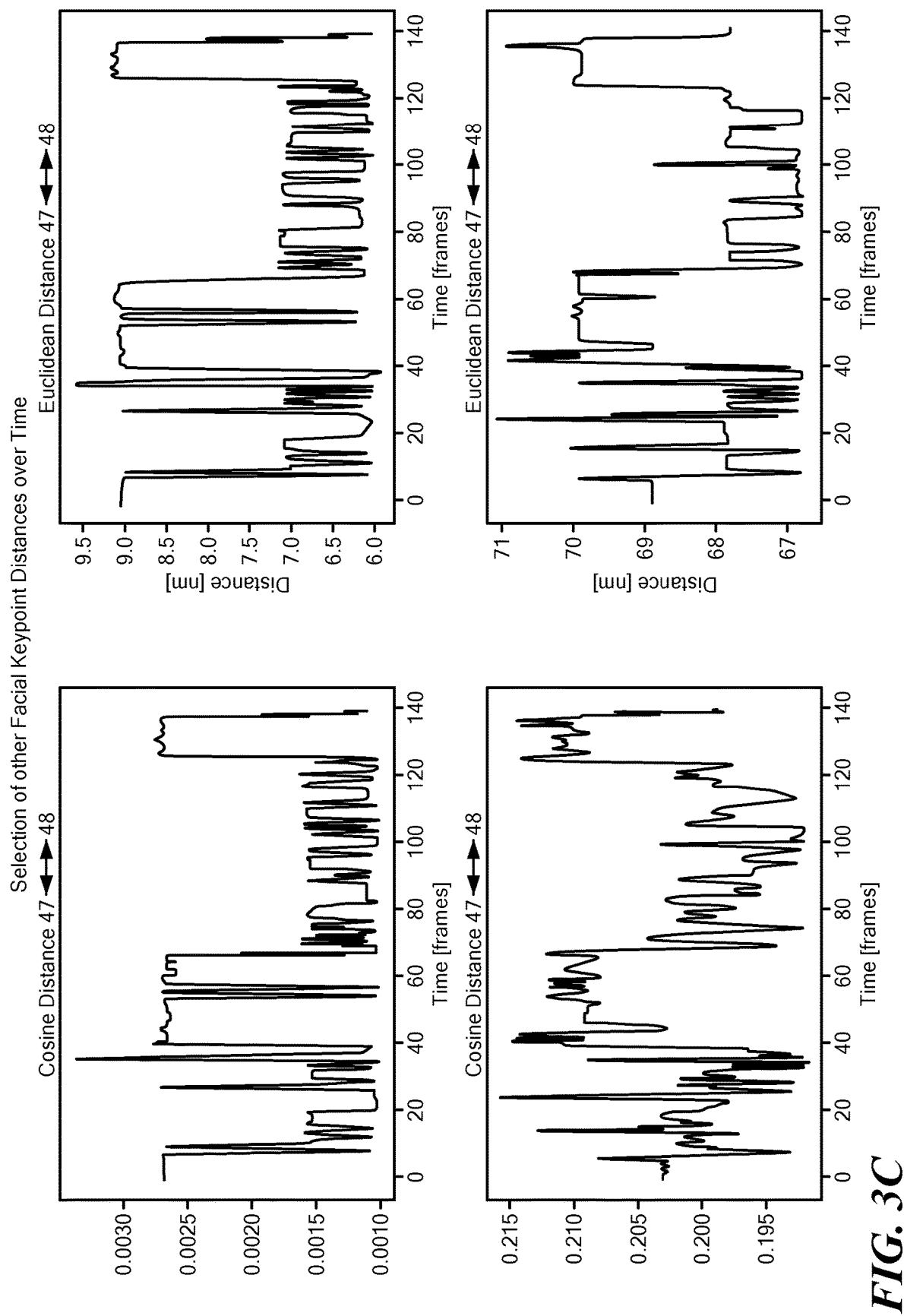
Figure 3D:
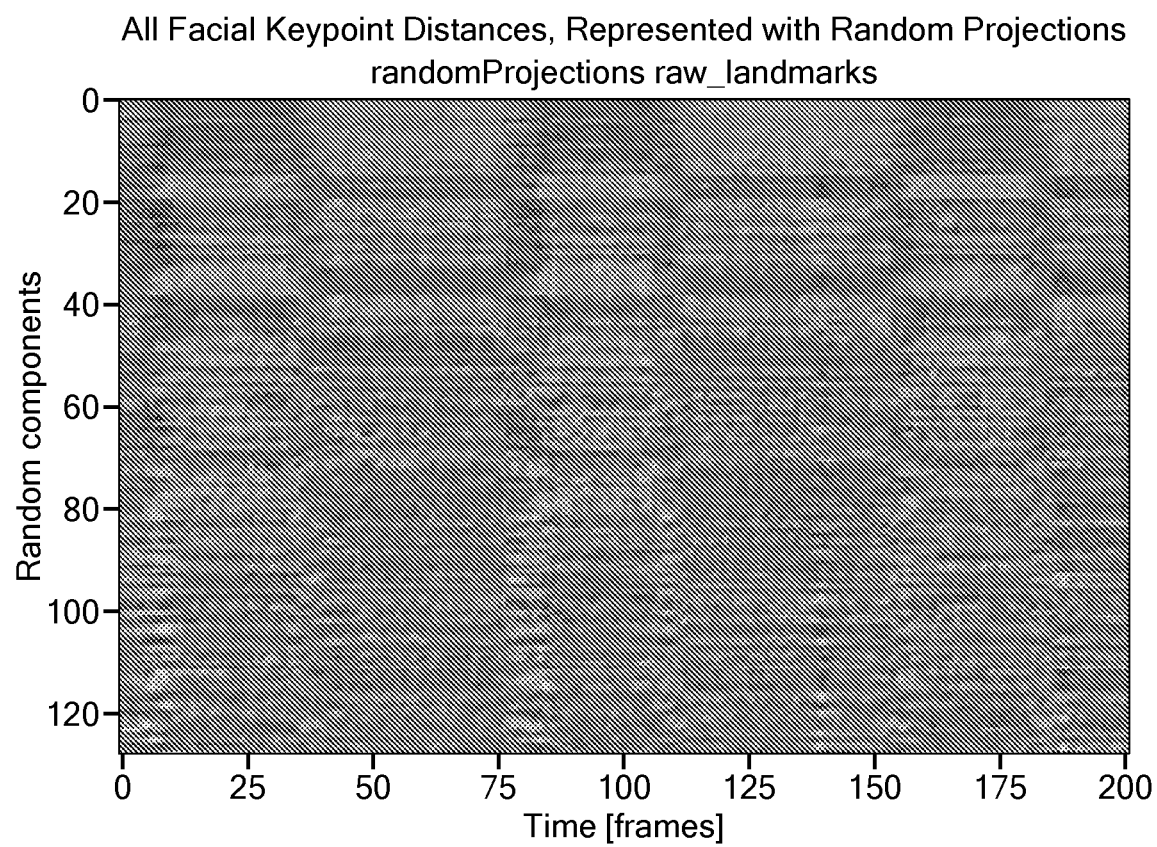

Using the face region images 210A/B/C, the system 100 may extract a representation of the person's facial gesture state (FIG. 3A). This may include extracting facial landmarks and keypoints as a collection of points. For example, the system 100 may extract the location of the nose 310, mouth 330 (including the upper lip 332 and lower lip 334), eyes 320A/B (including upper lids 322A/B and lower lids 324A/B, and jaw line 340). The system 100 may then plot the distances between these collection of points (e.g., between the top of eyelid and the bottom of the eyelid) as a function of time (FIG. 3B) including the cosine and Euclidian distances (FIG. 3C). Additionally or alternatively, the system 100 may also plot all facial keypoint distances as random projections (FIG. 3D).

Figure 4A:
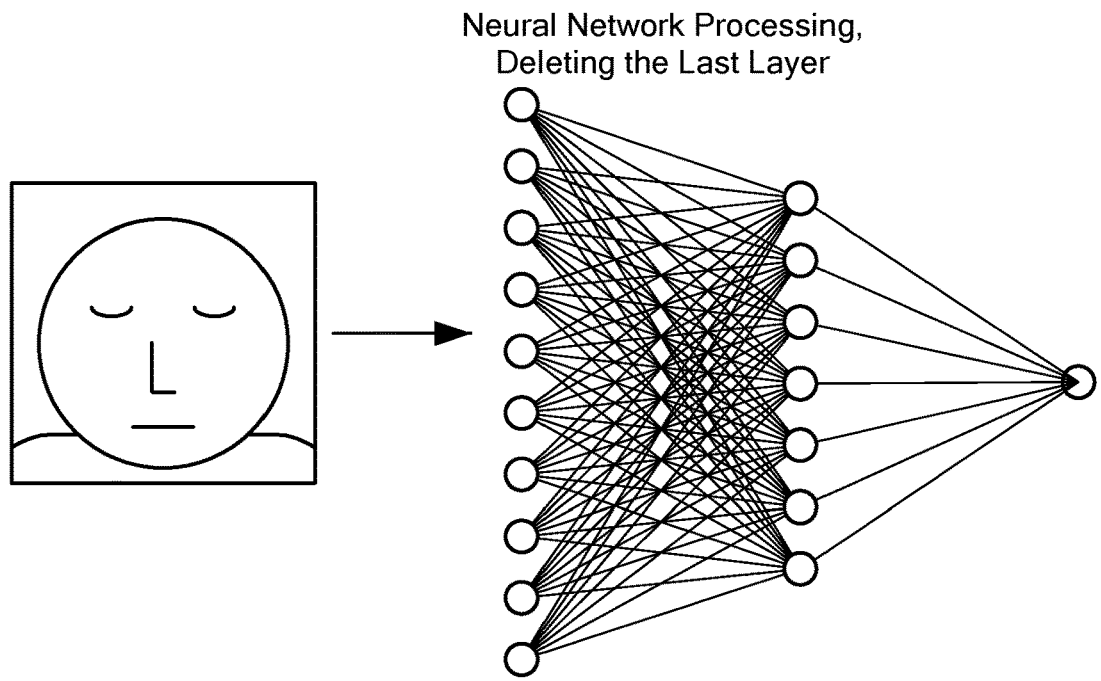
FIGS. 4A and 4B schematically show the neural network processing of images/videos taken with the system shown in FIG. 1, in accordance with illustrative embodiments of the present invention.
Figure 4B:
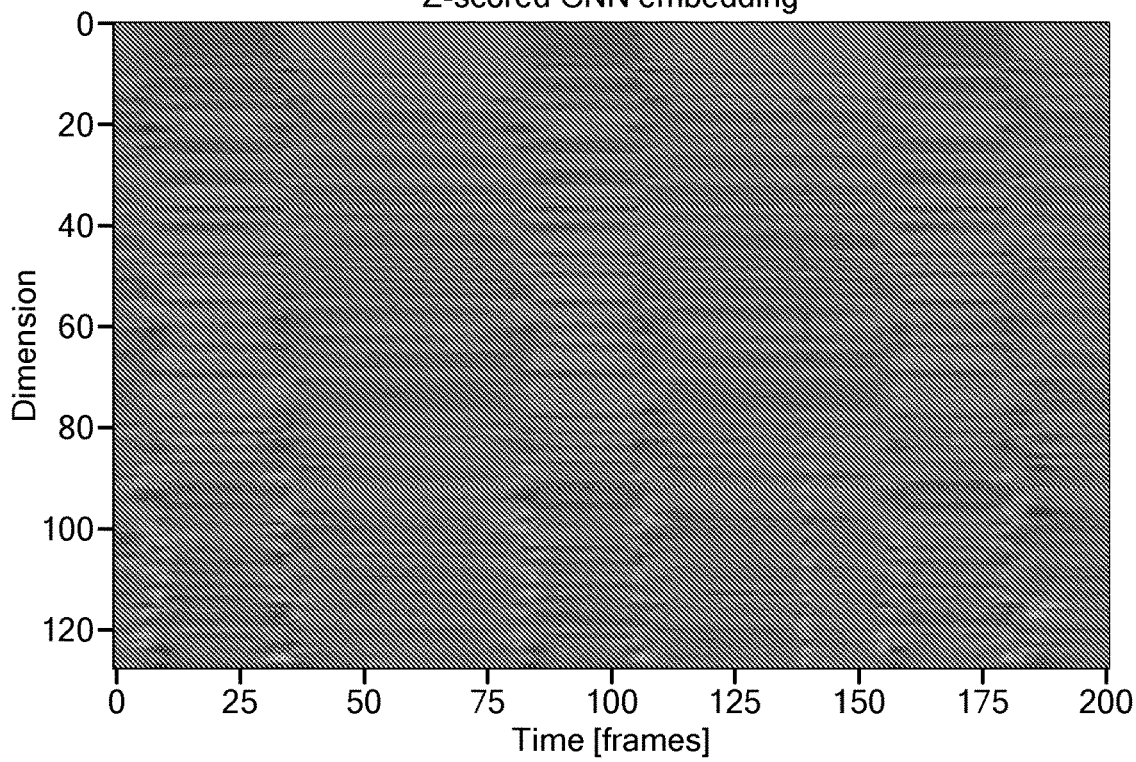

It is important to note that although the specific value of each of the keypoints and distances are different between each human subject, the characteristics of these features is common across all human subjects (or other subject of the same species). Additionally, some embodiments may utilize latent embeddings derived from artificial neural networks (FIGS. 4A and 4b) or "deep learning" models.

Figure 5:
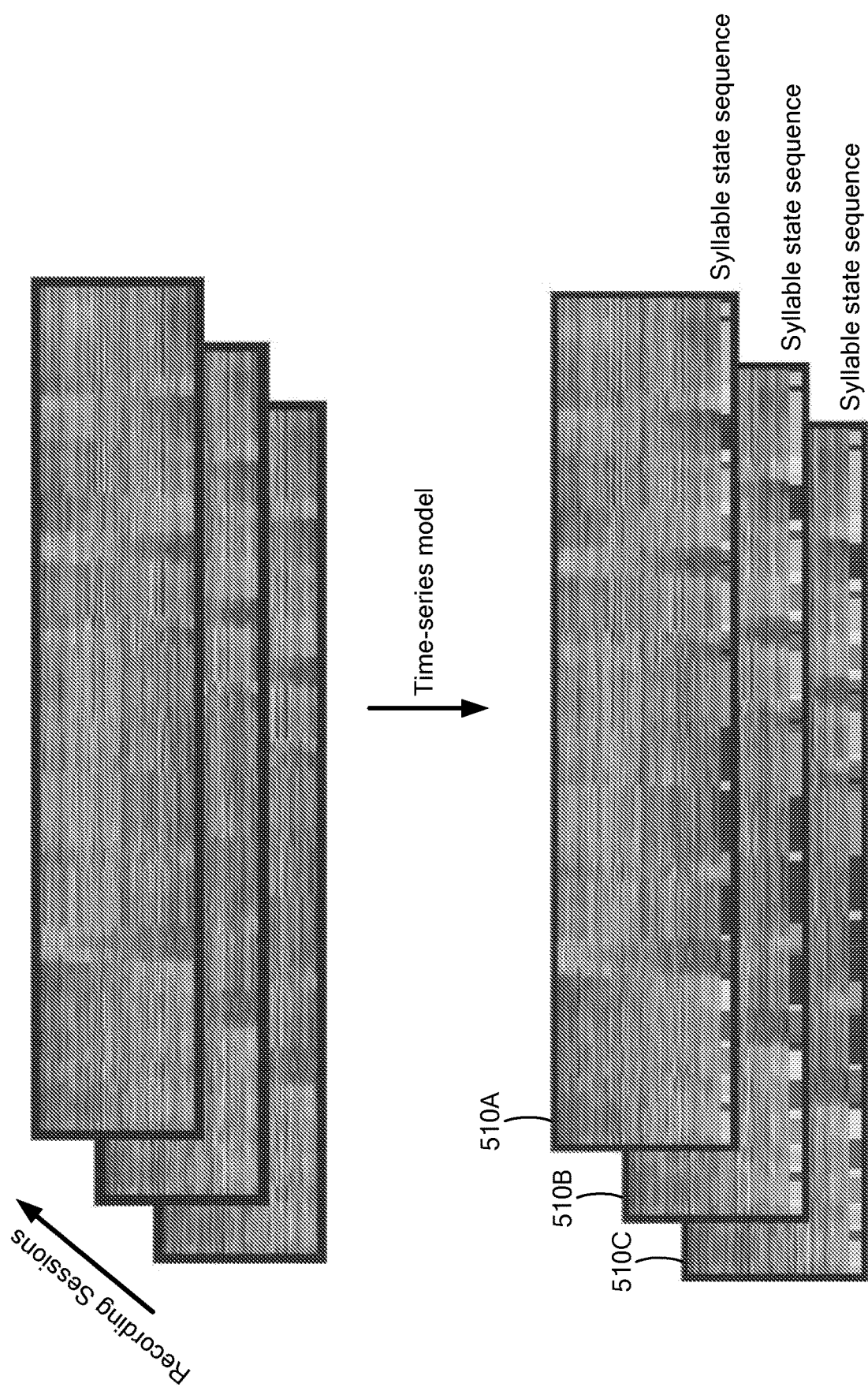
FIG. 5 schematically shows the generation of syllable state sequences from images taken with the system shown in FIG. 1, in accordance with illustrative embodiments of the present invention.

The system 100 may then save (e.g., locally on the computer 130 and/or in the centralized storage device/cloud 150) each of the above data streams (e.g., the head pose, eye gaze, facial gesture state, etc.) as separate data streams. The system may then concatenate each data stream so that they are aligned in time and combine the time-series data from multiple recordings of multiple human subjects (FIG. 5).

As noted above, various embodiments of the present invention identify "facial syllables" from the obtained video stream. To that end, the system 100 may apply a machine learning or statistical model to the collection of time-series models to identify the facial syllables from the video streams (e.g., without input or intervention from the user 140). The facial syllables are essentially the fundamental components of the various facial expressions/gestures and movements of the patient/subject 110 (e.g., the raising of an eyebrow, the upturn of the corner of the mouth, etc.). Once the facial syllables are discovered, they may be analyzed and inspected in order to be given plain-language names. For example, for each discovered facial syllable and for each example of a facial syllable, the original video may be extracted for that time point (e.g. the time at which the syllable occurred). The system 100 may then overlay the resulting videos (and/or display them side-by-side), to give the user 140 an intuitive understanding of what facial expression has been captured by that particular facial syllable. This may be repeated for all discovered facial syllables.

The system 100 may automatically discover the facial syllables using machine learning or statistical methods, including, but not limited to, time-series models, probabilistic graphical models, artificial neural networks, support vector machines, random forests, and k-nearest neighbor methods. In some embodiments, the system 100 can use an embellished hidden markov model (HMM) (e.g., a Sticky HDP-AR-HMM (Hierarchical Dirichlet Process, Autoregressive-emission Hidden Markov Model)). The HDP component is used to automatically discover the number of states, the AR component is used to model facial expressions as a smoothly varying trajectory over time, the HMM component models the grammatical structure, and the "Sticky" modifier to the HMM models the duration distribution of each facial syllable.

It should be noted that when discovering the facial syllables from the videos, the system 100 may analyze the videos in aggregate. For example, if sixty videos (e.g., each 1 minute in length) are entered into the system 100, the system 100 will analyze all sixty videos to determine what the common gestures/syllables are, how many there are, how the face moves over time and how long (e.g., the number of frames) the gesture lasts for each syllable. In some embodiments, the facial syllables will be discovered only when the data being analyzed shows the syllable in question over time (e.g., over multiple frames of the video). To that end, each discovered syllable will be representative of a gesture/expression that occurs over a time period (e.g., over a series of frames) as opposed to just a single frame. Additionally, one of the key factors is how each of the gestures relate over time. In this manner, the system 100 can learn in aggregate over all data and videos. Furthermore, each time a new patient/subject 110 is recorded and the videos saved, there is a new data point for the system to analyze and learn from.

Figure 6:
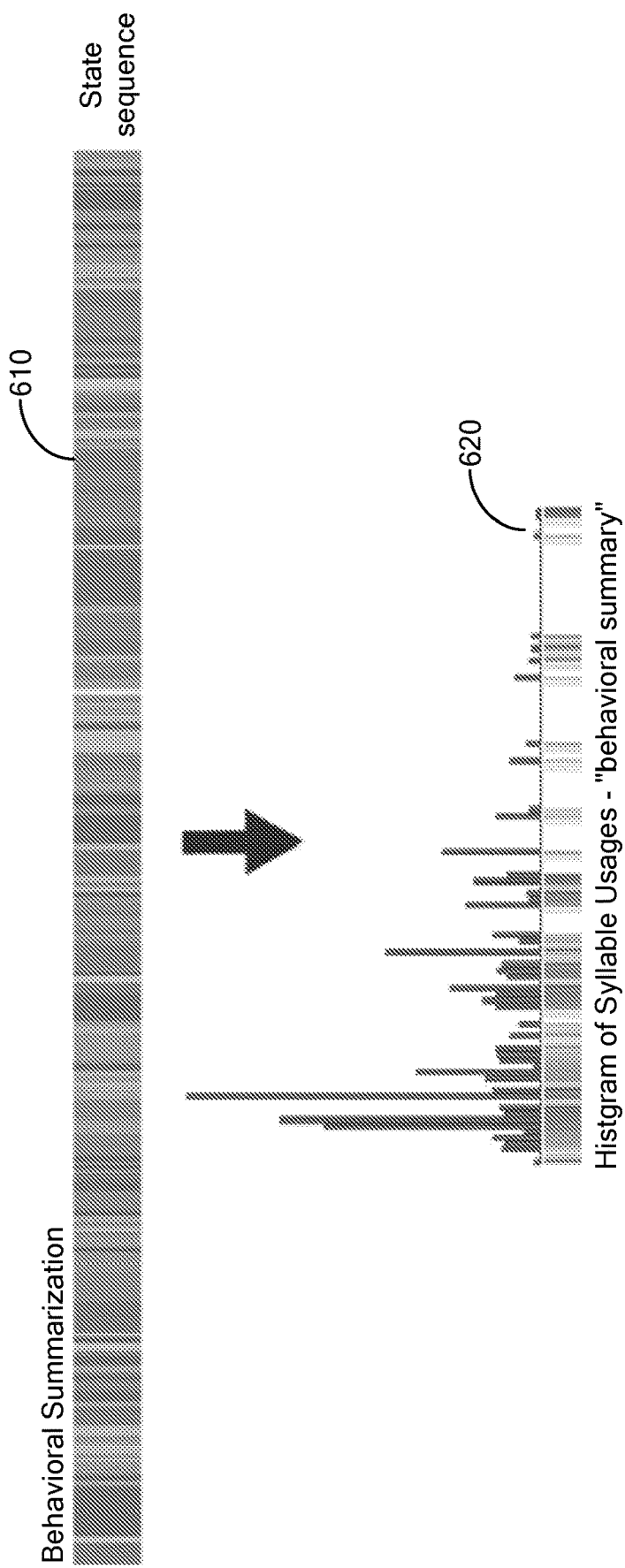
FIG. 6 shows the generation of a histogram of the syllable usages to represent a behavioral summary, in accordance with illustrative embodiments of the present invention.

Once the syllables have been identified, as shown in FIG. 5, the system 100 may compile the facial syllables into a series of state sequences 510A/B/C. The state sequences are a collection of syllables and represent a given state of the patient/subject (e.g., pain, no pain, the level of pain, happy, etc.). There are typically multiple state sequences (e.g., 20-60) in a given video and the state sequences allow the system 100 and/or user 140 to determine the condition of the patient/subject (e.g., whether they are in pain or not and/or the level of pain they are in). The system 100 may save the state sequences, and associate each discovered facial syllable with a given point in time (e.g., for a given time period/number of frames) in each video By counting how often each facial syllable occurs and creating a histogram 620 of the state frequencies for all discovered facial syllables, the system 100 may extract a behavioral "fingerprint" or summary from one or more state sequences 610 (FIG. 6). For example, the histogram may be calculated for each video recording, and it may be a fixed-length vector representation of how often each discovered facial expression is used in that particular video recording. In some embodiments and depending on the application, the histograms may be averaged over multiple recordings of an individual. This behavioral fingerprint may also be associated with other metadata attached to the video recording, such as the user's self-rated pain level. It should also be noted that, when counting how often each facial syllable occurs, the system 100 may also count the number of frames the patient/subject 110 was in a given state (e.g., the number of frames the patient/subject 110 is grimacing, the number of frames the patient/subject 110 is smiling, etc.). This provides a summary of the subject's state over a given time period (e.g., a summary over 30 seconds that the subject 110 is not in pain or at a low level of pain, a summary of when the subject 110 is in pain or at a given level of pain, etc.).

Figure 7A:
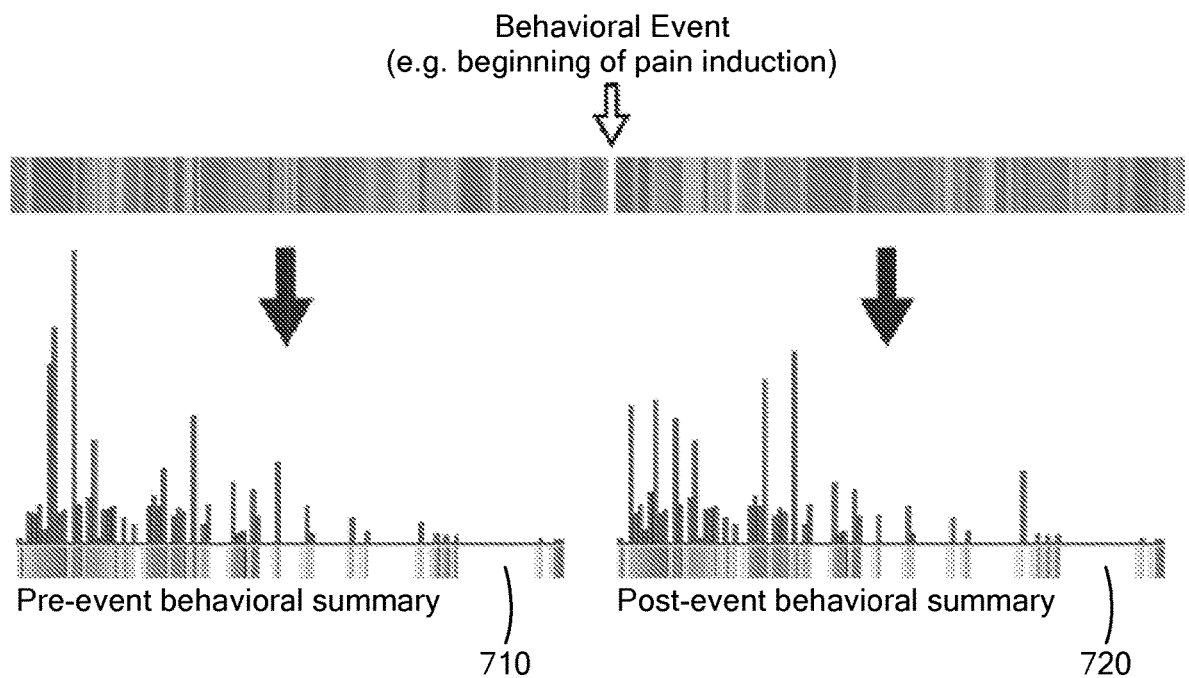
FIGS. 7A and 7B schematically show the identification and classification of pre and post event behavioral summaries, in accordance with illustrative embodiments of the present invention.
Figure 7B:
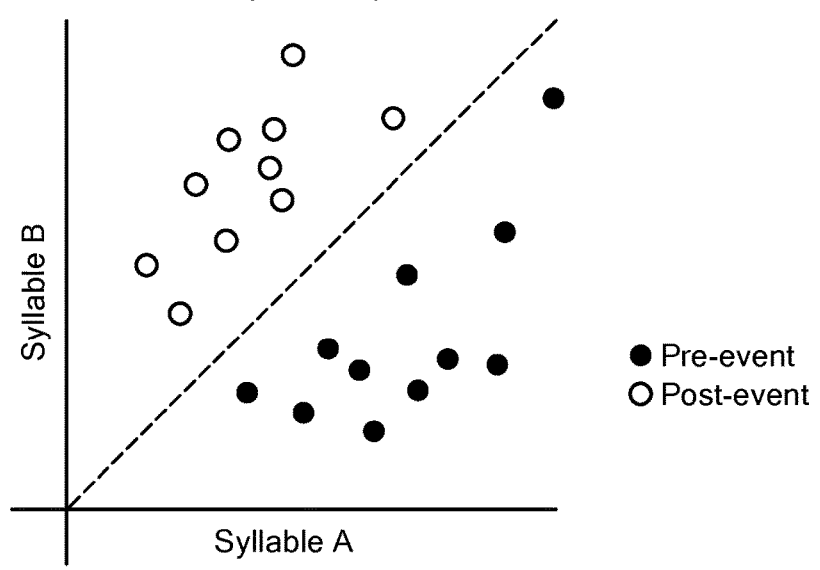

As shown in FIG. 7A, the system 100 may create multiple histograms. For example, the system 100 may create a pre-event behavioral summary 710 and a post event behavioral summary 720. As the names suggest, pre-event behavioral summary summarizes the subject's behavior prior to the event (e.g., prior to performing the task, prior to being given pain medication, etc.) and the post event behavioral summary 720 summarizes the subject's behavior after the event occurred (e.g., after performing the task, after being given pain medication, etc.). The system 100 may then classify each of the summaries into pre and post event classes (FIG. 7B) that the system 100 may later use for predictions (discussed in greater detail below).

As noted above, the behavioral fingerprint may be associated with the metadata within the video. In such embodiments, the system 100 may use the metadata and the behavioral fingerprint 620 to construct statistical models that predict the metadata using only the behavioral fingerprint. For instance, if a patient/subject 110 provided a report of the pain level that they experienced during a video recording, the system 100 may regress the extracted behavioral fingerprint against their reported pain level. In order to learn this association, the system 100 may use linear models, such as logistic regression (for discrete or ordinal metadata), linear regression (for continuously varying metadata), and/or random forest based models. Additionally or alternatively, the system 100 may also employ more sophisticated machine learning techniques as appropriate, such as support vector machines, gradient-boosted decision trees, neural networks, or Gaussian processes, to name but a few. Based on the above, the system 100 may then predict the patient's state (e.g., the patient's level of pain on a scale of 1-10) and determine/detect what pain looks like for a given subject 110.

Using the information gathered/determined by the system 100, the decision support device 170 may then take the appropriate action and/or create the appropriate alert/output. For example, as discussed above, the device 170 may send the output to the clinical trial evaluation system, or generate alarm to alert a patient of a potential medical episode, alert a driver that they are experiencing heightened anxiety of fatigue while driving, and/or trigger the start of a treatment for a dementia patient about to experience an anger episode, etc.

It is important to note that, although the system 100 is described above as performing the analysis in a "batch-type" manner, the system 100 may also perform the analysis in real-time. For example, the system 100 may have a "real-time" and/or "streaming data" mode of assessment. When in the real time/streaming data mode, and after having identified the syllables and motif of syllables for a set of emotional states (e.g., from previous batch analyses), the system 100 can classify a single human subject as being in a particular state by mapping/finding previously identified syllables or motifs of syllables in the video stream of the subject.

Various embodiments of the above systems and methods may be used in numerous applications. For example, the system 100 may be used by doctors prescribing pain medications such as opioids. In such applications, the system 100 may predict a patient's level of pain, irrespective of their self-reported level of pain. This will allow doctors to more confidently prescribe opioid based pain medicine and decrease the risk of prescribing such medications to those individuals who do not need it but may be self-reporting a high level of pain (e.g., in order to obtain the medication).

Moreover, in drug development applications, the system 100 may be used to determine how well a new drug candidate works. For example, during drug testing and/or clinical trials, the user 140 may ask the subject 110 to perform a task and record the subject to determine a pre-dose level of pain. The user 140 may then give the subject 110 the medication, wait an appropriate period of time (e.g., however long the user 140 expects the drug to take to work) and ask the subject 110 to perform the task again. The system 100 may then determine the post-dose level of pain and compare the pre-dose level of pain to the post-dose level of pain to determine how well the drug worked, without relying on the patient/subject's self-reported levels of pain (which may be subjective and/or vary).

The system 100 may also be beneficial when selecting candidates for drug and clinical trials. In particular, the user 140 may record perspective candidates performing various tasks. The system 100 may then analyze the videos of each the perspective candidates, look at the different levels of pain (or other criteria) for each of the candidates, and interpret what they report as pain levels. The user 140 and/or the system 100 may then use this information to determine which candidates will be right for the drug trial. Additionally or alternatively, the system 100 may use the information to look for a certain biomarker and/or generate a score for each candidate.

In addition to the level of pain, some embodiments of the present invention may be used to determine and predict the source and/or mechanism of the pain. For example, different types of pain (sharp, dull, acute, chronic, etc.) and source/mechanisms of pain (e.g., muscular, nerve, joint, bone, etc.) will cause different reactions by the patient. By analyzing the video, the system 100 may be able to help determine the source and mechanism of the pain, allowing the doctor to develop a more targeted/successful treatment plan. Furthermore, in some instances, the system 100 may be connected to and/or used in conjunction with other devices. For example, the system 100 may be connected to a drug delivery device and the system 100 may be used to control the drug delivery device to meter pain medication (or other medication) to the subject 110 based on the video analysis. Additionally or alternatively, the system 100 may be used in conjunction with other monitoring equipment such a blood flow rate monitors, blood pressure monitors, and EKGs, to name but a few. The data from each of these pieces of monitoring equipment (e.g., the subject's blood flow rate, changes in blood pressure, etc.) may be incorporated into the analysis and used to help determine the facial syllables, state sequences, pain levels, etc. This other data may be incorporated during the initial analysis or within the decision support device 170.

The embodiments described above provide numerous advantages over prior art systems. For example, by discovering the various features/criteria discussed above (e.g., facial syllables, state sequences, etc.) across multiple frames of the videos (e.g., over time), various embodiments of the present invention are able to discover the correct time structure to use in the analysis based on the data rather than simply using a scanning window (e.g., merely deciding on a time window a priori). Additionally, embodiments of the present invention are able integrate features (whether as features extracted from the video only, or combining video features with non-video features, such as other physiological measurements, mentioned above) by modeling them together without prior specification of their biological relationships. This is in contract to prior art systems, that utilize a post hoc integration method and apply a set of weighting to combine different features (blood flow rate, action units, and EEG, etc.) into a score.

It should be noted that although the system 100 is described above as being used for humans and in relation to pain management, the system 100 may be used in other applications such as depression, neuro-degenerative diseases, the diagnosis of post-traumatic stress disorder ("PTSD"), sleep analysis studies, and determining behavioral states. For example, the system 100 may be used to determine a level of anxiety, depression, anxiety, etc. In sleep analysis applications, the system may analyze video of the subject sleeping and identify fine features in the subject's sleep movement beyond restlessness. Such analysis may also useful in the diagnosis of PTSD, as early symptoms of PTSD may manifest during sleep. Also in PTSD diagnosis applications, the system may analyze the expressions/movements of the subject while awake to look for signs the subject may be suffering from PTSD. Additionally, the system may be used for other areas of the body besides the face (e.g., arms, legs, hips, back, hands, feet, etc.). Furthermore, the system 100 may be used for animals (e.g., cows, pigs, dogs, etc.).

In other embodiments, the system 100 may be used to authenticate video streams and detect deepfakes (e.g., fake videos in which a person in the video is replaced with someone else's likeness). For example, the system 100 may be used to review/analyze a real video of a person (e.g., a celebrity) to determine a syllable profile of the individual. The system 100 may then analyze addition videos purported to be of the same individual to compare the syllable profile of the actual individual against the new video. If the syllable profiles between the two videos match, then the video may be authenticated (e.g., the system 100 may confirm that the video is of the actual person and not a fake video). Conversely, if the system 100 determines that the syllable profiles do not match, the videos are fakes.

Example 1: Predicting/Quantifying Pain

Data: The experiment analyzed 178 human annotated and previously recorded pain study videos. The videos included 25 unique individuals with 5 reported acute pain levels when the individuals were asked to perform a task (e.g., raising their arm).

Figure 8:
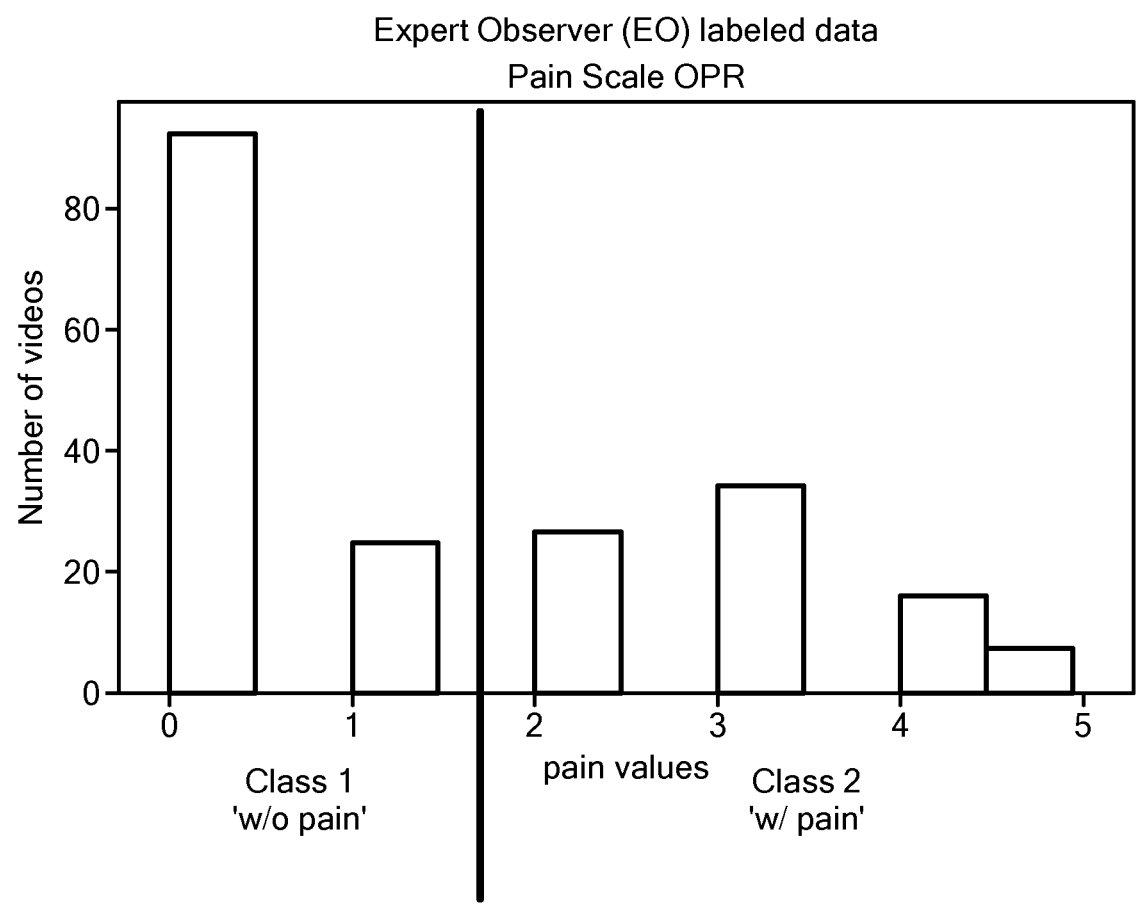
FIG. 8 schematically shows the scoring of the video streams of example 1 by an expert observer and the classification into "with" and "without" pain groups, in accordance with some embodiments of the present invention.

Methods and Modeling: Using the systems and methods described herein, 128 facial features were extracted and facial syllables were determined for each video. The syllables were then submitted to a classifier to identify the pain states. Additionally, an expert observer scored each of the videos from 0 to 5, with 5 being the highest level of pain. The videos were then grouped into two classes. One class was labeled as "with pain" and the other class was labelled "without pain." (see FIG. 8) The videos (e.g., frames of the video) were also analyzed using a Facial Action Coding System (FACS) to determine current action units.

Figure 9A:
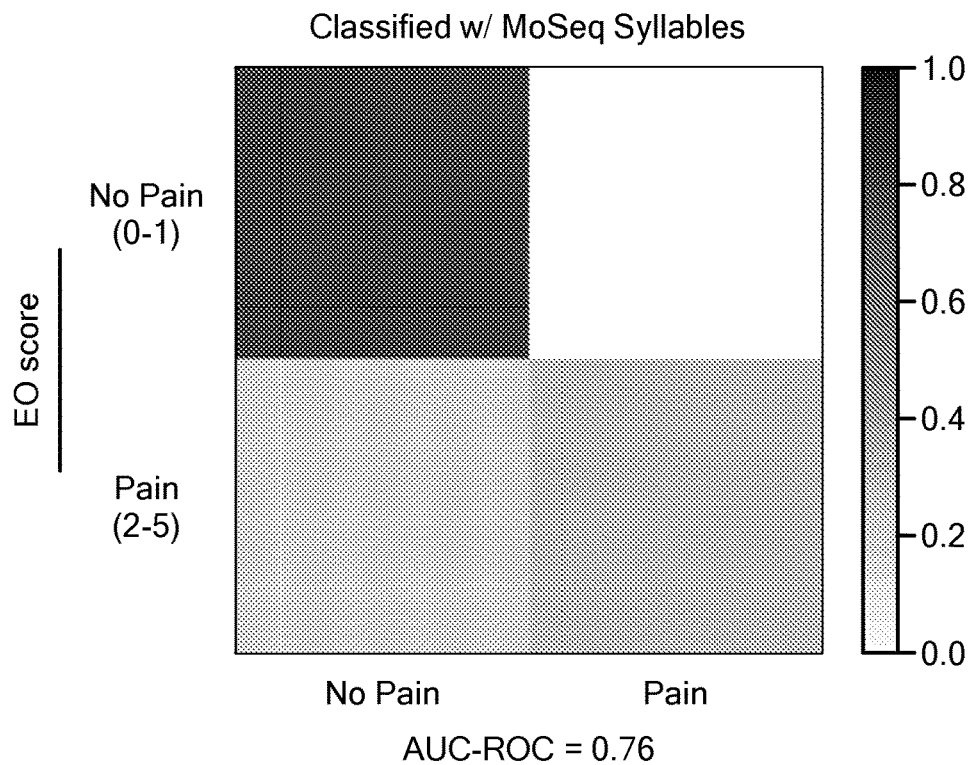
FIGS. 9A and 9B schematically show the classification of the video streams of example 1 by various embodiments of the present invention and by a Facial Action Coding System ("FACS").
Figure 9B:
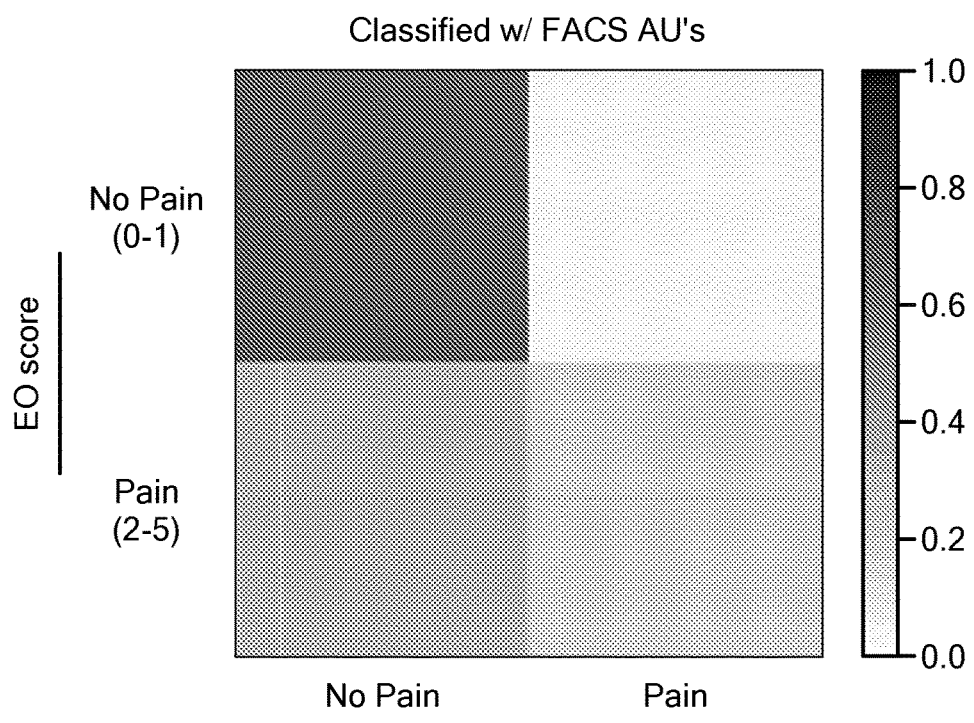

Results: The results of the analysis using the systems and methods described herein were compared to the analysis performed by the FACS and the expert observer. In each case, the systems and methods described herein were able to determine shared syllables across all individuals. As a result, the systems/methods described herein were able to outperform the FACS system (see FIGS. 9A and 9B) and the expert observer in determining a level of pain. For example, as shown in FIG. 9A, the systems and methods described herein are generalizable to new faces (e.g., when overlaps are removed from the training set to the test set) resulting in a more accurate representation of the subject's pain level (e.g., the area under the curve ("AUC-ROC") for the present system/methods is 0.76 as compared to 0.66 for the classification performed by the FACS action units). Similarly, as shown in FIG. 9B, the present system/method is more sensitive than the FACs action units (e.g., the area under the curve ("AUC-ROC") for the present system/methods is 0.99 as compared to 0.76 for the classification performed by the FACS action units)

Example 2: Determining A Placebo Effect

Figure 10:
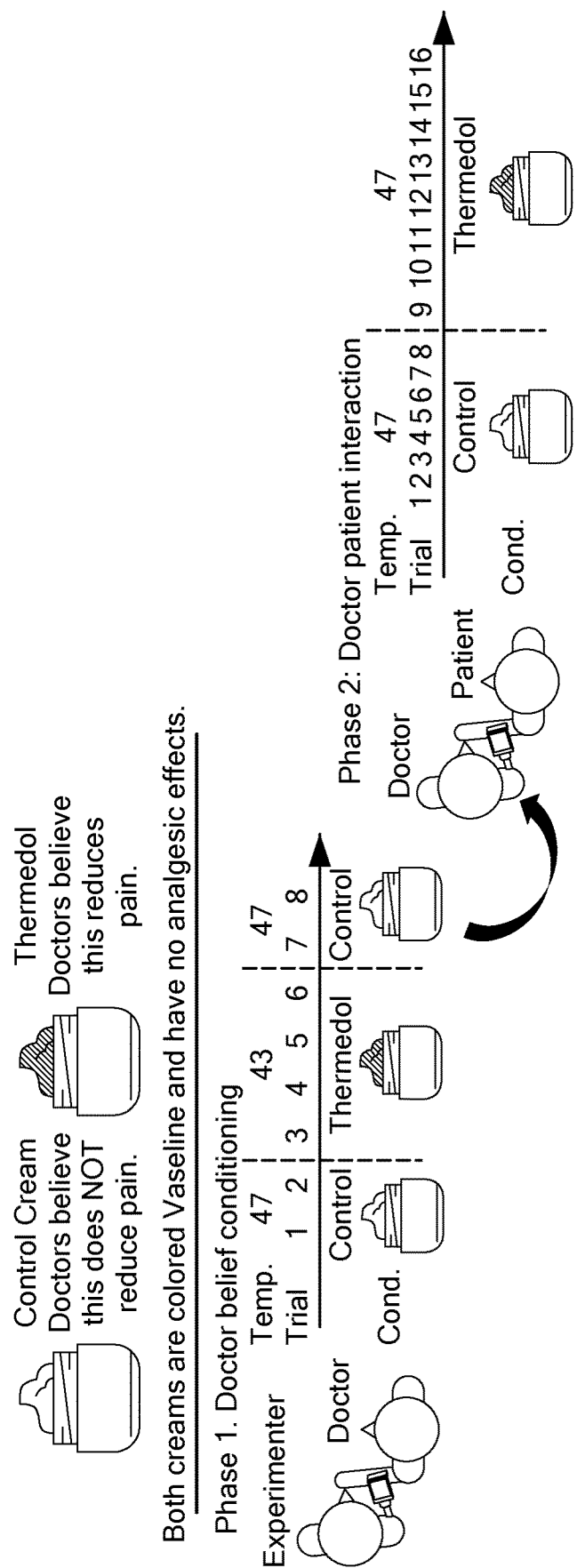
FIG. 10 schematically shows phase 1 and phase 2 of experiment 2, in accordance with various embodiments of the present invention.

Stage 1—Doctor Belief Conditioning: In the first stage, two creams were applied to the hands of a group of doctors and their hands were placed on a hot plate. The doctors were told the first cream is a placebo and the second cream is an analgesic that reduces pain. However, neither cream had any analgesic effects and were merely colored petroleum jelly. In order to condition the doctors to believe that the second cream did reduce pain, the temperature on the hot plate was turned down (e.g., 43 degrees vs. 47 degrees) when the second cream was applied to the doctor so that the doctor's felt less pain/discomfort as compared to when the first/control cream was applied (see FIG. 10).

Stage 2—Doctor Patient Interaction: In the second stage, each of the doctors was instructed to apply either the first/control cream or the second cream on the patient and to tell the patient that they were applying a pain cream. The hands of each of the patients were then placed on the hot plate in a manner similar to the doctors during the conditioning step. However, the hot plate was set to the same temperature for both the patients receiving the first/control cream (the cream the doctor believes to be a placebo) and the patients receiving the second cream (the cream the doctor believes to be an analgesic). Despite neither cream having analgesic properties, the patients' reported a lower pain level with the second cream indicating that there is a placebo effect for the second cream.

Figure 11:
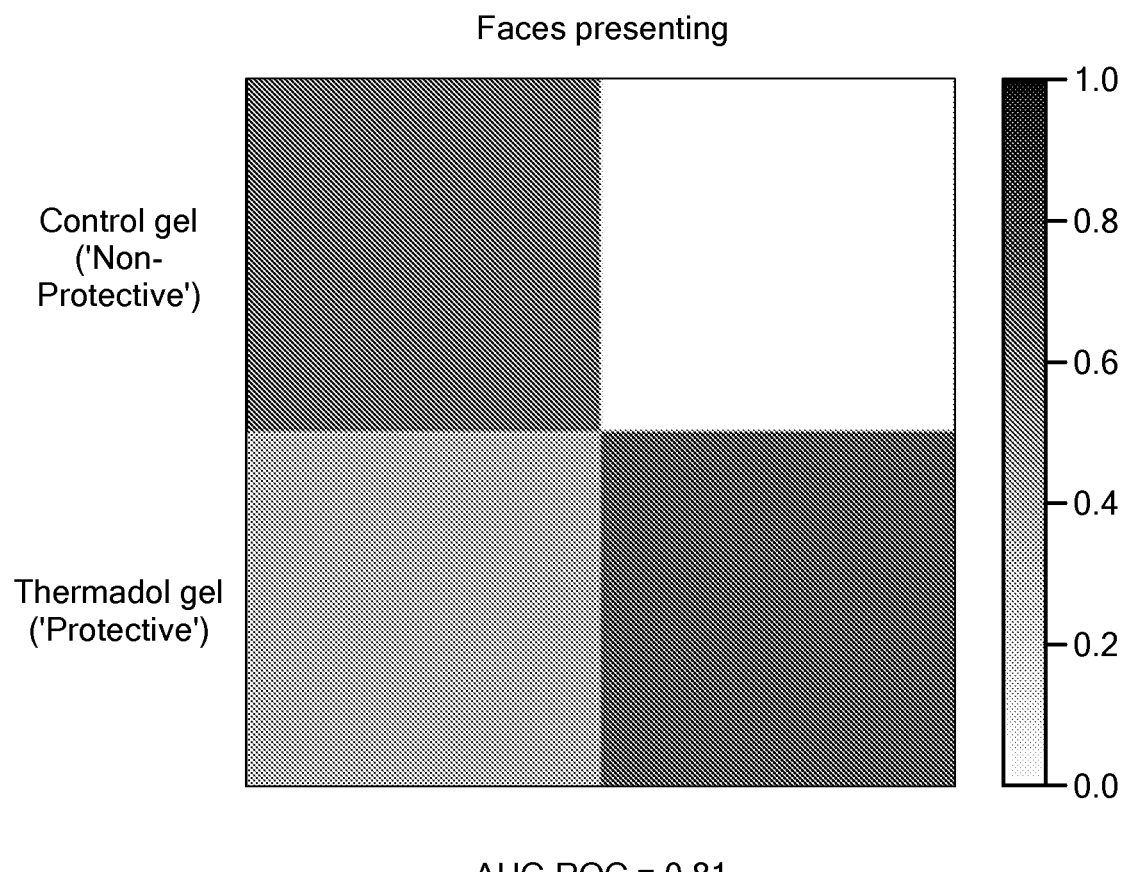
FIG. 11 schematically shows the results of experiment 2, in accordance with some embodiments of the present invention.

Analysis/Results: While administering each of the creams, video of the doctors' faces were taken and analyzed using the system/methods described herein to determine the facial syllables/profile of the doctor. In each case, the system/method was able to detect that the doctors were subconsciously emitting different facial syllables when applying the first/control cream as compared to when applying the second cream (see FIG. 11). The subconscious facial syllables emitted by the doctors reflected a belief or confidence that the second cream would work and/or guilt or lying that the first/control cream was not going to work, resulting in the above mentioned placebo effect. It is important to note that such information (e.g., whether a doctor/technician is subconsciously signaling a patient/subject that a drug/medicine is expected to work and/or not work) is useful in clinical trial settings or similar settings where a placebo effect may impact the results of testing (e.g., to ensure that the doctors/technicians are not subconsciously impacting the results of the study).

It should be noted that the representations of the system described above are a significantly simplified representation of the system. Those skilled in the art should understand that such a device has many other physical and functional components, such as central processing units, packet processing modules, and short-term memory. Accordingly, this discussion is in no way intended to suggest that FIGS. 1-11 represents all of the elements of the system 100.

It should also be noted that FIG. 1 only schematically shows each of these components. Those skilled in the art should understand that each of these components can be implemented in a variety of conventional manners, such as by using hardware, software, or a combination of hardware and software, across one or more other functional components. For example, various components may be implemented using a plurality of microprocessors executing firmware. As another example, the components may be implemented using one or more application specific integrated circuits (i.e., "ASICs") and related software, or a combination of ASICs, discrete electronic components (e.g., transistors), and microprocessors. Accordingly, the representation of the components is for simplicity purposes only. In fact, in some embodiments, the functionality of the components may be distributed across a plurality of different machines—not necessarily within the same device.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as a pre-configured, stand-along hardware element and/or as preprogrammed hardware elements (e.g., application specific integrated circuits, FPGAs, and digital signal processors), or other related components.

In an alternative embodiment, the disclosed apparatus and methods (e.g., see the various flow charts described above) may be implemented as a computer program product for use with a computer system. Such implementation may include a series of computer instructions fixed either on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the invention may be implemented as a combination of both software (e.g., a computer program product) and hardware. Still other embodiments of the invention are implemented as entirely hardware, or entirely software.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A system for facial analysis comprising:
a camera configured to take a video of a subject's face, the video having a plurality of frames;
a data storage device configured to receive and store the video; and
a data processing system having a processor and program code which when executed:
  (a) generates a pose data stream by extracting, from the plurality of frames, a plurality of poses of the subject's face, each pose of the plurality of poses including an angle and a position of the subject's face,
  (b) generates a facial gestures state data stream by extracting, from the plurality of frames, a plurality of representations of the subject's facial gesture state, each representation of the plurality of representations including facial keypoints, the facial keypoints being a collection of points on the subject's face,
  (c) concatenates the pose data stream and the facial gestures state data stream to align the data streams in time,
  (d) extracts a plurality of facial syllables from the aligned data streams,
  (e) compiles the plurality of facial syllables into a series of state sequences, and
  (f) extracts a behavioral fingerprint for the subject based on the series of state sequences, the behavioral fingerprint providing a summary of the subject's state over a given period of time, wherein extracting the behavioral fingerprint includes calculating a histogram of state frequencies based on the series of state sequences, the histogram indicative of how often each of the plurality of facial syllables occurs in the series of state sequences.

2. A system according to claim 1, wherein the camera is a two-dimensional camera or a three-dimensional camera.

3. A system according to claim 1, wherein the data processing system also has program code that extracts a face region from each of the frames of the video prior to extracting the pose of the subject's face.

4. A system according to claim 1, wherein the facial keypoints include at least one selected from the group consisting of the subject's nose, mouth, eyes and jaw line.

5. A system according to claim 1, wherein the data processing system uses latent embeddings derived from artificial neural networks and/or deep learning models to extract the facial gesture state.

6. A system according to claim 1, wherein the processing system is configured to analyze videos in aggregate to extract the facial syllables.

7. A system according to claim 1, wherein the processing system is configured to predict, based on the behavioral fingerprint, at least one selected from the group consisting of a level of pain, a level of anxiety, a level of depression, a level of hunger, a level of satiety, and a level of fatigue.

8. A system according to claim 1, wherein the processing system is configured to classify the behavioral summary as a pre-event summary or a post event summary.

9. The system according to claim 1, wherein extracting the plurality of facial syllables includes applying a sticky hierarchical Dirichlet process (HDP), autoregressive-emission (AR) hidden Markov model (HMM), wherein an HDP component is usable to automatically discover the number of states, an AR component is usable to model facial expressions as a smoothly varying trajectory over time, an HMM component is usable to model a grammatical structure between syllables, and a sticky modifier to the HMM is usable to model syllable durations.

10. A method of facial analysis comprising:
recording a video of a subject's face using a camera, the video having a plurality of frames;
storing the video in a data storage device;
generating a pose data stream by extracting, from the plurality of frames, a plurality of poses of the subject's face, each pose of the plurality of poses including an angle and a position of the subject's face;
generating a facial gestures state data stream by extracting, from the plurality of frames, a plurality of representations of the subject's facial gesture state, each representation of the plurality of representations including facial keypoints, the facial keypoints being a collection of points on the subject's face;
concatenating the pose data stream and the facial gestures state data stream to align the data streams in time;
extracting a plurality of facial syllables from the aligned data streams;
compiling the plurality of facial syllables into a series of state sequences; and
extracting a behavioral fingerprint for the subject based on the series of state sequences, the behavioral fingerprint providing a summary of the subject's state over a given period of time, wherein extracting the behavioral fingerprint includes calculating a histogram of state frequencies based on the series of state sequences, the histogram indicative of how often each of the plurality of facial syllables occurs in the series of state sequences.

11. A method according to claim 10, wherein the camera is a two-dimensional camera or a three-dimensional camera.

12. A method according to claim 10, further comprising:
extracting a face region from each of the frames of the video prior to extracting the pose of the subject's face.

13. A method according to claim 10, wherein the facial keypoints include at least one selected from the group consisting of the subject's nose, mouth, eyes and jaw line.

14. A method according to claim 10, wherein extracting the facial gesture state includes using latent embeddings derived from artificial neural networks and/or deep learning models to extract the facial gesture state.

15. A method according to claim 10, wherein extracting the facial syllables includes analyzing videos in aggregate.

16. A method according to claim 10, further comprising predicting, based on the behavioral fingerprint, at least one selected from the group consisting of a level of pain, a level of anxiety, a level of depression, a level of hunger, a level of satiety, and a level of fatigue.

17. A method according to claim 10, further comprising classifying the behavioral summary as a pre-event summary or a post event summary.

18. The method according to claim 10, wherein extracting the plurality of facial syllables includes applying a sticky hierarchical Dirichlet process (HDP), autoregressive-emission (AR) hidden Markov model (HMM), wherein an HDP component is usable to automatically discover the number of states, an AR component is usable to model facial expressions as a smoothly varying trajectory over time, an HMM component is usable to model a grammatical structure between syllables, and a sticky modifier to the HMM is usable to model syllable durations.

19. A system for subject analysis comprising:
a camera configured to take a video of a portion of a subject, the video having a plurality of frames;
a data storage device configured to receive and store the video; and
a data processing system having a processor and program code which when executed:
(a) generates a pose data stream by extracting, from the plurality of frames, a plurality of poses of the portion of the subject, each pose of the plurality of poses including an angle and a position of the portion of the subject,
(b) generates a gestures state data stream by extracting, from the plurality of frames, a plurality of representations of the subject's gesture state, each representation of the plurality of representations including keypoints, the keypoints being a collection of points on the portion of the subject,
(c) concatenates the pose data stream and the gestures state data stream to align the data streams in time,
(d) extracts a plurality of syllables from the aligned data streams,
(e) compiles the plurality of syllables into a series of state sequences, and
(f) extracts a behavioral fingerprint for the subject based on the series of state sequences, the behavioral fingerprint providing a summary of the subject's state over a given period of time, wherein extracting the behavioral fingerprint includes calculating a histogram of state frequencies based on the series of state sequences, the histogram indicative of how often each of the plurality of syllables occurs in the series of state sequences.

20. A system according to claim 19, wherein the camera is a two-dimensional camera or a three-dimensional camera.

21. A system according to claim 19, wherein the portion of the subject is the subject's face.

22. A system according to claim 21, wherein the pose of the portion of the subject is the pose of the subject's face, the pose including the angle and position of the subject's face.

23. A system according to claim 22, wherein the representation of the subject's gesture state is a representation of the subject's facial gesture state, the keypoints being facial keypoints that are a collection of points on the subject's face.

24. A system according to claim 23, wherein the plurality of syllables are a plurality of facial syllables.

25. A system according to claim 23, wherein the facial keypoints include at least one selected from the group consisting of the subject's nose, mouth, eyes and jaw line.

26. A system according to claim 19, wherein the data processing system use latent embeddings derived from artificial neural networks and/or deep learning models to extract the gesture state.

27. A system according to claim 19, wherein the processing system is configured to analyze videos in aggregate to extract the syllables.

28. A system according to claim 19, wherein the processing system is configured to predict, based on the behavioral fingerprint, at least one selected from the group consisting of a level of pain based, a level of anxiety, a level of depression, a level of hunger, a level of satiety, and a level of fatigue.

29. A system according to claim 19, wherein the processing system is configured to classify the behavioral summary as a pre-event summary or a post event summary.

30. A system according to claim 19, wherein the data processing system also has program code that extracts a region from each of the frames of the video prior to extracting the pose of the portion of the subject.

31. The system according to claim 19, wherein extracting the plurality of facial syllables includes applying a sticky hierarchical Dirichlet process (HDP), autoregressive-emission (AR) hidden Markov model (HMM), wherein an HDP component is usable to automatically discover the number of states, an AR component is usable to model facial expressions as a smoothly varying trajectory over time, an HMM component is usable to model a grammatical structure between syllables, and a sticky modifier to the HMM is usable to model syllable durations.

* * * * *